(12) United States Patent
Cherry, Sr. et al.

(10) Patent No.: US 9,976,770 B2
(45) Date of Patent: May 22, 2018

(54) EXHAUST FILTER MODULE, AND A METHOD AND APPARATUS FOR EFFICIENCY TESTING THE SAME

(75) Inventors: John L. Cherry, Sr., Washington, NC (US); Sean O'Reilly, Morristown, NJ (US); Mark Huza, Columbia, MD (US); Thomas C. Morse, Greenville, NC (US)

(73) Assignee: CAMFIL USA, INC., Riverdale, NJ (US)

( * ) Notice: Subject to any disclaimer, the term of this patent is extended or adjusted under 35 U.S.C. 154(b) by 2337 days.

(21) Appl. No.: 11/277,079

(22) Filed: Mar. 21, 2006

(65) Prior Publication Data

US 2006/0276120 A1 Dec. 7, 2006

Related U.S. Application Data

(60) Provisional application No. 60/663,833, filed on Mar. 21, 2005.

(51) Int. Cl.
| | | |
|---|---|---|
| *H05K 7/20* | (2006.01) | |
| *F24F 13/28* | (2006.01) | |
| *F24F 11/00* | (2018.01) | |
| *G01N 1/22* | (2006.01) | |

(52) U.S. Cl.
CPC .......... *F24F 13/28* (2013.01); *F24F 11/0009* (2013.01); *F24F 2011/0093* (2013.01); *G01N 1/22* (2013.01)

(58) Field of Classification Search
CPC ...................................................... F24F 13/28
USPC ....... 454/339; 73/865.9, 432.1, 159, 863.23; 340/605, 607; 96/417; 55/467
See application file for complete search history.

(56) References Cited

U.S. PATENT DOCUMENTS

| | | | |
|---|---|---|---|
| 3,614,421 A | | 10/1971 | Alter et al. |
| 4,191,543 A | * | 3/1980 | Peters .............................. 96/223 |
| 4,371,386 A | * | 2/1983 | DeVecchi ........................ 55/338 |
| 4,494,403 A | * | 1/1985 | Bowers .............. B01D 46/0006 73/40.7 |
| 4,515,007 A | * | 5/1985 | Herman ................... G01M 3/20 55/DIG. 9 |
| RE31,952 E | * | 7/1985 | Wilcox .............. B01D 46/0004 239/514 |

(Continued)

FOREIGN PATENT DOCUMENTS

JP     2002177716 A    6/2002

OTHER PUBLICATIONS

PCT Search Report from PCT/US06/10497 dated Sep. 14, 2007, copy consists of 8 unnumbered pages.

(Continued)

*Primary Examiner* — Steven B McAllister
*Assistant Examiner* — Samantha Miller
(74) *Attorney, Agent, or Firm* — Patterson + Sheridan, LLP

(57) ABSTRACT

A filter module configured for exhaust application, and a method and apparatus for testing the same are provided. In one embodiment, the filter module includes a downstream sampling port configured to allow a technician to sample flow, downstream of the filter module, from the cleanroom side of a filter module. In another embodiment, a shroud adapted to sealing engage a filter module under test is provided and includes a tube, disposed in the shroud, that couples a port to a downstream sampling port of the filter module.

16 Claims, 3 Drawing Sheets

(56) References Cited

U.S. PATENT DOCUMENTS

| | | | |
|---|---|---|---|
| 4,955,997 A * | 9/1990 | Robertson, III | 96/138 |
| 5,256,375 A | 10/1993 | Morris | |
| 5,417,610 A * | 5/1995 | Spransy | 454/187 |
| 5,810,657 A | 9/1998 | Pariseau | |
| 5,922,095 A * | 7/1999 | Hustvedt et al. | 55/385.1 |
| 5,964,910 A * | 10/1999 | Keele | 55/385.1 |
| 6,193,603 B1 * | 2/2001 | Tai | 454/300 |
| 6,200,367 B1 * | 3/2001 | Phillips | B01D 39/2034 55/301 |
| 6,264,551 B1 * | 7/2001 | Smith | 454/248 |
| 6,321,637 B1 * | 11/2001 | Shanks et al. | 95/273 |
| 6,471,582 B1 | 10/2002 | Tucker | |
| 6,572,468 B1 * | 6/2003 | Sasaki et al. | 454/187 |
| 6,835,128 B1 * | 12/2004 | Olson | 454/232 |
| 7,186,286 B2 * | 3/2007 | Morse | B01D 46/0086 55/417 |
| 7,210,363 B2 * | 5/2007 | Morse | G01M 3/3281 55/385.3 |
| 7,310,228 B2 * | 12/2007 | Chen | 361/695 |
| 7,658,787 B2 * | 2/2010 | Morse | B01D 46/0086 55/385.2 |
| 8,133,310 B2 * | 3/2012 | Huza | B01D 46/0028 55/309 |
| 2002/0073842 A1 * | 6/2002 | Gruber | B01D 46/0086 95/1 |
| 2004/0047776 A1 | 3/2004 | Thomsen | |
| 2005/0000901 A1 | 1/2005 | Campbell et al. | |
| 2007/0144119 A1 * | 6/2007 | Bauer | 55/385.2 |
| 2008/0216457 A1 * | 9/2008 | Morse | B01D 46/008 55/502 |
| 2011/0107917 A1 * | 5/2011 | Morse | B01D 46/0091 96/417 |

OTHER PUBLICATIONS

Camfil Farr, Inc. Pharmaseal® Roomside Replaceable Ducted Ceiling Module Brochure, Product Sheet, pp. 1-8, date unknown.
Official Letter dated May 6, 2014 from European Patent Office for corresponding European Patent Application No. 207789.

* cited by examiner

EXHAUST FILTER MODULE, AND A METHOD AND APPARATUS FOR EFFICIENCY TESTING THE SAME

CROSS-REFERENCE TO RELATED APPLICATIONS

This application claims benefit of U.S. Provisional Patent Application Ser. No. 60/663,833, filed Mar. 21, 2005, which is herein incorporated by reference in its entirety.

BACKGROUND OF THE INVENTION

Field of the Invention

Embodiments of the invention generally relate to a filter module configured for exhaust applications, and a method and apparatus for testing the same.

Description of the Related Art

In many cleanroom and contaminant applications, filter modules are often utilized in an exhaust configuration to remove air or other fluids from rooms or equipment. In many of these applications, regulations, certifications and/or process protocols require that the filter be tested for overall efficiency after installation into the module. However, testing a filter module in this manner is a difficult challenge. Particularly, the interstitial space defined between the housing and the filter disposed therein often cannot be readily accessed by a technician. Thus, downstream sampling of the installed exhaust filter often cannot be performed. Additionally, sampling within the interstitial space defined between the housing of the module and the filter may not be accurate due to poor mixing of air within the filter housing. Thus, testing of an installed exhaust filter is usually performed in the reverse flow direction to facilitate downstream sampling from the cleanroom side of the filter. This manner of testing is controversial, as many believe that some pinhole filter leaks are flow direction dependent, and as such, a filter passing an efficiency test with air flowing in a first direction, may fail when the flow through the filter is reversed to the direction used during operation of the filter of the cleanroom. As leaking filters may pose health hazards, allow downstream contamination and present regulatory issues or other undesirable problems, it is highly desirable to test filters in the same flow direction utilized during normal filter operation.

Thus, there is a need for a method and apparatus for efficiency testing of a filter installed in an exhaust housing.

SUMMARY OF THE INVENTION

A filter module configured for exhaust application, and a method and apparatus for testing the same are provided. In one embodiment, an exhaust filter module includes a downstream sampling port configured to allow a technician to sample flow, downstream of the filter module, from the cleanroom side of a filter module.

In another embodiment, an apparatus for testing the filter module includes a shroud mounted to the cleanroom side of a filter module. The shroud includes a flange for sealing against the face of the filter module and a collar for coupling to a duct coupled to a blower. In one embodiment, two sample ports are formed through the shroud. A first port is configured to sample air in the volume defined between the shroud and the face of a filter element. The second port is coupled to a conduit which is routed through the shroud to a penetration of the filter module. The penetration couples the second port to a downstream sampling port which may be disposed downstream of the filter module, for example, within the duct work coupling the filter module to an exhaust blower. The shroud may optionally include an aerosol injection port. The aerosol injection port may be coupled to an aerosol dispersion device, such as a perforated tube. Baffles or other mixing elements may be disposed in the shroud to mix the aerosol so that a uniform challenge is provided to the face of the filter element.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, wherever possible, to designate identical elements that are common to the figures. It is contemplated that some elements of one embodiment may be beneficially incorporated in other embodiments.

DETAILED DESCRIPTION

The method and apparatus for testing a filter module configured for exhaust applications is provided. The filter module itself is designed and engineered to allow for "roomside" measurement of overall filter efficiency in exhaust applications. This is not possible with conventional wall and ceiling-mounted systems because overall efficiency measurements require samples to be taken from upstream and downstream of the filter. Downstream ductwork is generally not accessible from the roomside because it is located in interstitial spaces behind hard ceilings or walls. The filter module is designed to provide the necessary connections to allow for overall efficiency measurement from the room.

Figure 1:
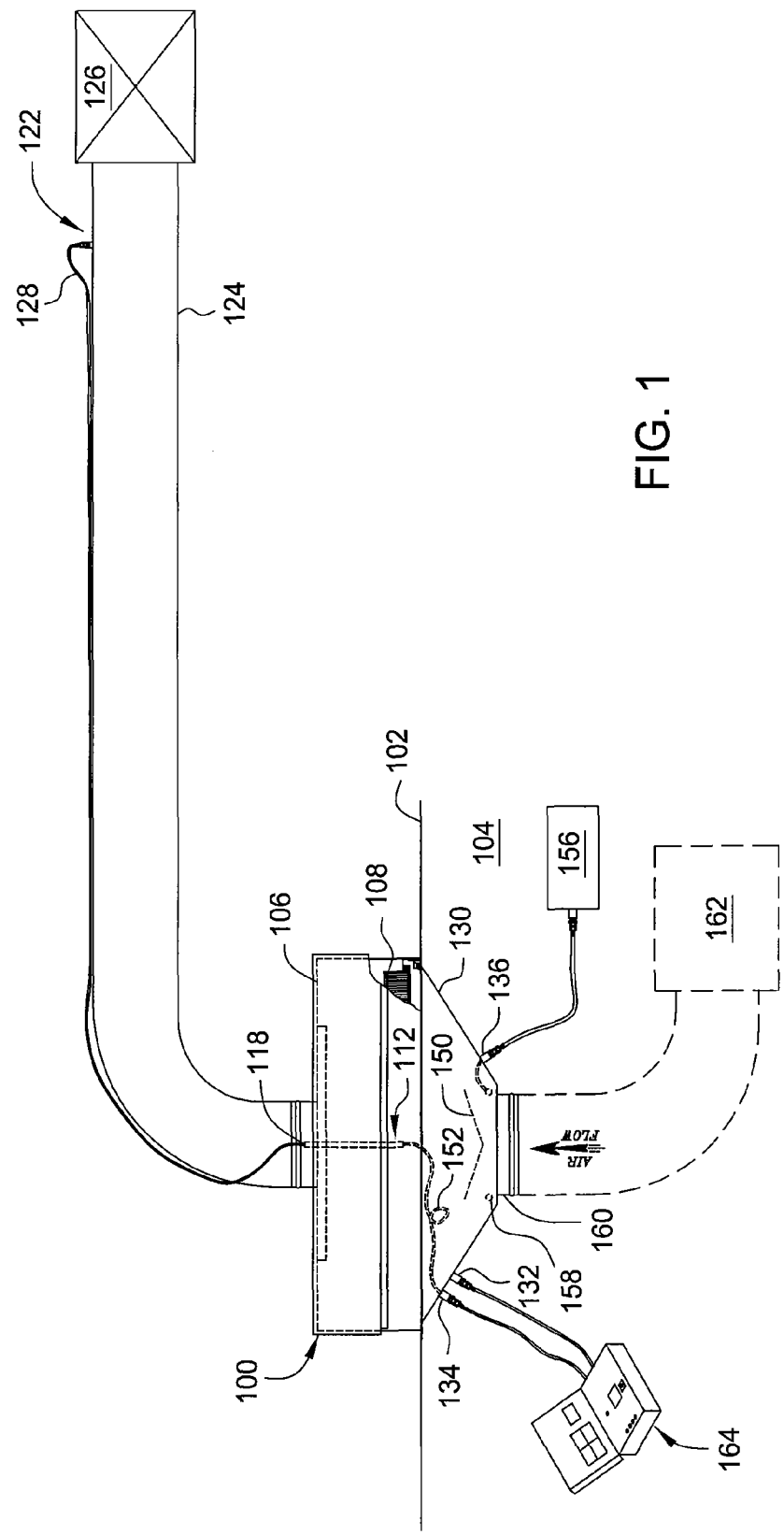
FIG. 1 depicts one embodiment of an apparatus for efficiency testing engaged with an exhaust filter module disposed in a ceiling of a cleanroom.
Figure 2:
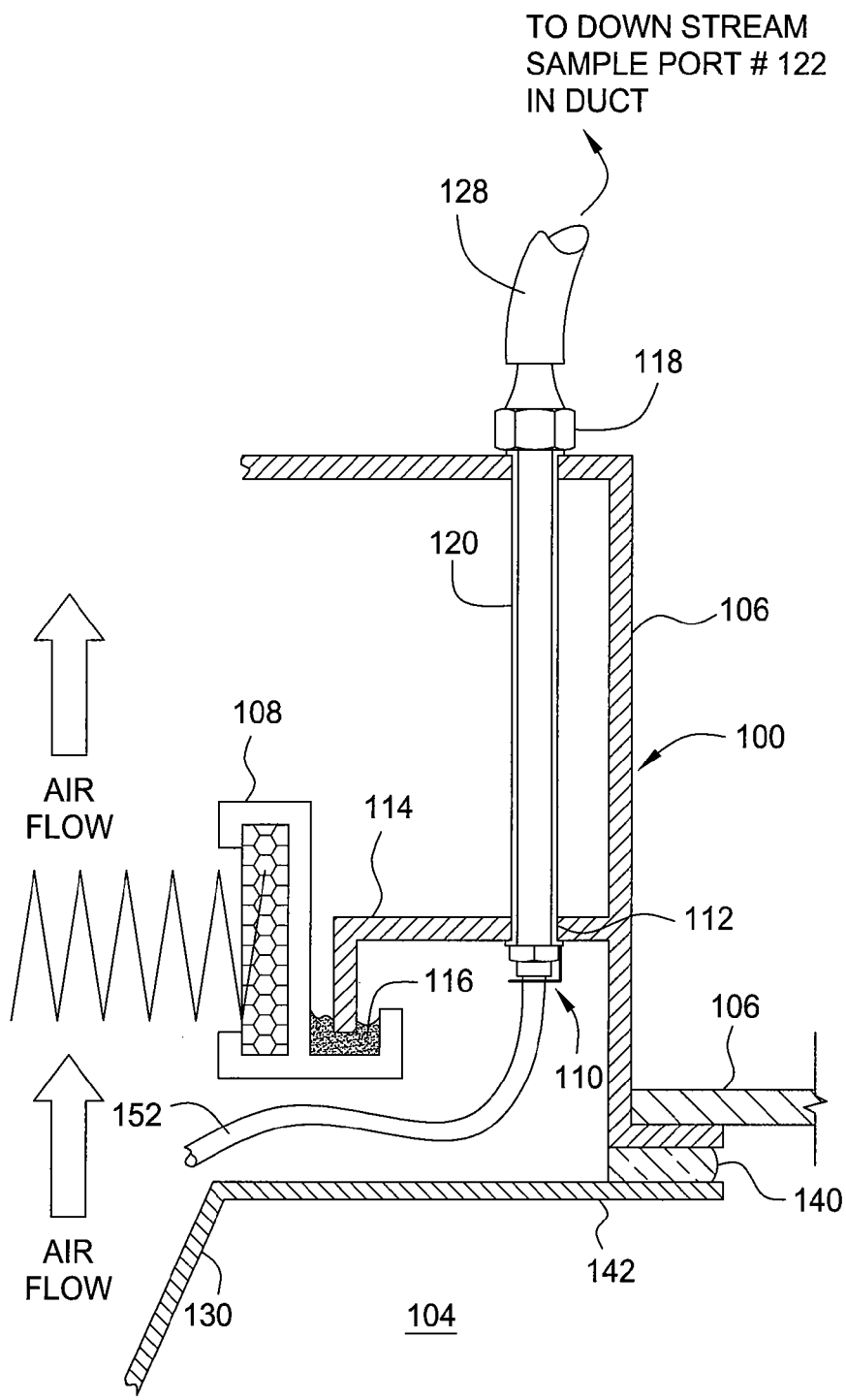
FIGS. 2-3 is a partial sectional views of the filter module of FIG. 1.
Figure 3:
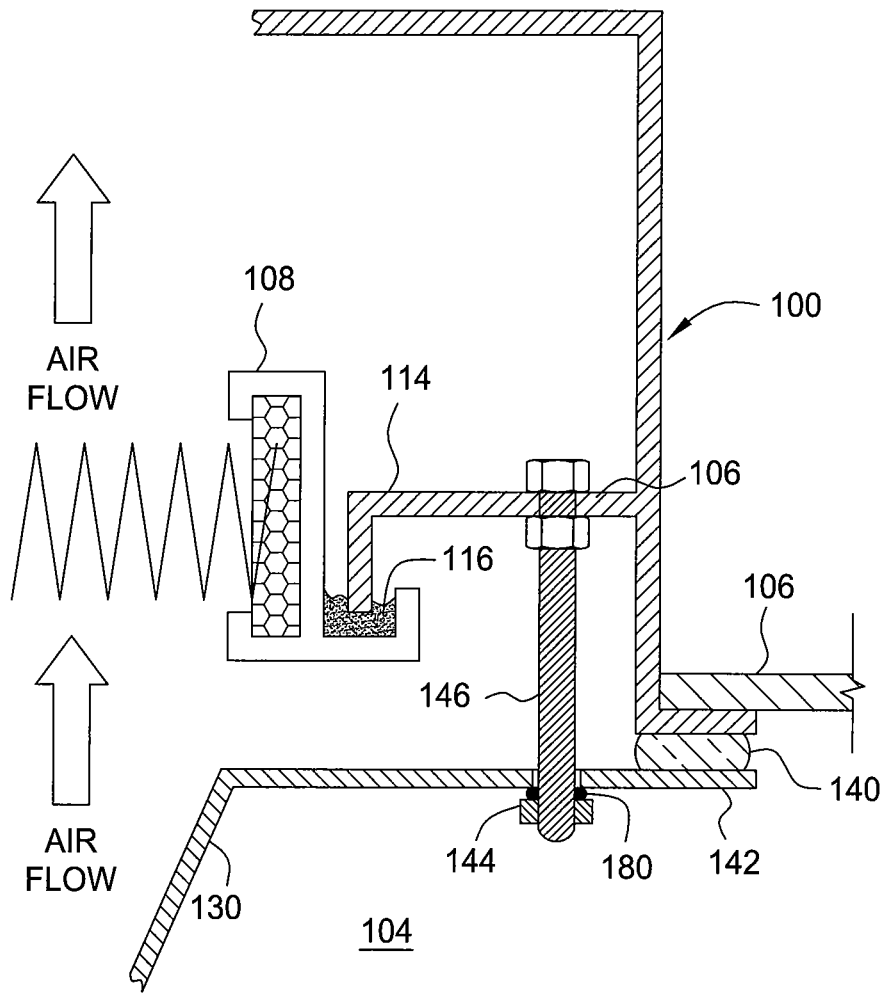

FIG. 1 depicts one embodiment of a filter module 100 configured for room exhaust applications mounting in a structure, for example, a wall, floor or ceiling 102 of a cleanroom 104. Additional partial sectional views of the filter modules 100 are depicted in FIGS. 1-3. One filter module that may be adapted to benefit from the invention is the PHARMASEAL® Hood, available from Camfil Farr, Inc., of Riverdale, N.J. It is contemplated that the filter module 100 may alternatively be mounting in the floor or wall of the cleanroom 104, or other equipment or mini-environments.

The filter module 100 includes a hood or housing 106 which holds a replaceable filter element 108. The housing 106 has filter-housing sealing interface that sealingly engages the filter element 108 to prevent air leakage between the housing 106 and filter element 108. In one embodiment, the filter-housing sealing interface is a knife-edge flange 114 extending from the housing 106 that sealingly engages a fluid seal 116 of the filter element 108. It is contemplated that the filter element 108 and housing 106 may alternately be sealed by other methods, for example, by a gasket or other seal.

A room-side downstream sampling port 112 is provided through the knife-edge flange 114, and in one embodiment, is in the form of a quick-disconnect fitting 110. The quick-disconnect fitting 110 is coupled to a ceiling-side downstream sampling port 118 located, in one embodiment, on the top of the filter module 100 by a tube 120. The ceiling-side downstream sampling port 118 includes a compression or other suitable fitting disposed on the exterior of the housing 106. Alternatively, the downstream sampling port 112 may be formed through a centerboard of the filter element 108, be disposed in the ceiling 102 of the cleanroom 104, or other suitable location.

The tube 120 generally provides a conduit through the interior portion of the housing 106, thereby allowing gases to pass between the interior of the cleanroom 104 and the area above the ceiling 102 via ports 112,118 while maintaining fluid isolation with the interior of the housing 106. The tube 120 may be rigid or flexible. In one embodiment, the tube 120 is metal and sealed to the housing 106 at each end.

A sampling port 122 is disposed in a ductwork 124 coupling the filter module 100 to an exhaust blower 126. The port 122 is disposed at a location sufficiently downstream of the filter module 100 to ensure adequate mixing of fluid (i.e., air and/or other exhaust gases). In one embodiment, the port 122 is located about 10 duct diameters downstream of the filter module 100. The sampling port 122 is connected to the compression fitting of the ceiling-side downstream sampling port 118 of the filter module 100 using tubing 128. This enables technicians to obtain a downstream sample of fluid passing through the filter as shown from the room side of the filter element 108.

To facilitate challenging the filter element 108 installed in the housing 106 from the room side of the filter module 100, a light-weight, removable shroud 130 is configured to attach to the filter module 100 from the room side. The shroud 130 may seal against the filter module 100 or the filter element 108. In one embodiment, a gasket 140 is disposed between a flange 142 of the shroud 130 and the filter module 100. The shroud 130 is compressed against the filter module 100 to form a seal. In the embodiment depicted in FIG. 3, a nut 144 is threaded on a stud 146 extending from the filter module 100 to urge the flange 142 against the filter module 100, and thus, to compress the gasket 140. An o-ring or other gasket 180 may be used to seal the nut 144 to the shroud 130. It is contemplated that the shroud 130 may be sealed to the filter module 100, filter element 108 and/or ceiling 102 using fluid seals, bladders, clamps, magnets or other suitable device.

The shroud 130 includes a plurality of ports, and a collar 160 disposed opposite the flange 142. The collar 160 may optionally be coupled to a blower 162 to provide a test flow through the shroud 130 and through the filter element 108 as shown by the arrows in FIGS. 1-2. In one embodiment, the collar 160 has a 12-inch (304.8 mm). Alternatively, the exhaust blower 126 may be utilized to provide the fluid flow through the filter module 100. In the embodiment depicted FIG. 1, three ports 132, 134, 136 are formed through the shroud 130. Each port 132, 134, 136 may be configured with a quick disconnect fitting or other suitable fitting to enable coupling of instruments, aerosol generators and the like to the ports. In one embodiment, each port 132, 134, 136 includes a ⅜-inch NPT chrome-plated brass quick disconnect.

The first and second ports 132, 134 allow the shroud to be coupled to a measuring device 164, such a photometer or particle counter, to enable efficiency testing of the filter element 108. The first port 132 is configured to allow an upstream sample to be taken from the plenum defined between the shroud 130 and the filter module 100. The shroud 130 may also include baffles or other mixing elements 150 (shown in phantom) to ensure the upstream sample is well mixed and representative of the concentration of particulate (e.g., aerosol challenge) present in the fluid directed through the shroud 130 and through the filter element 108.

The second port 134 is coupled to a small "patch cord" or flexible tube 152 disposed in the interior of the shroud 130. The tube 152 has a sufficient length to extend and allow connection of the second port 134 to the downstream sampling port 112 located on the knife-edge flange 114. This flexible tube 152 is connected prior to sealing the shroud 130 to the filter module 100. This allows a downstream measurement to be taken by the measuring device 164 through the port 122.

The third port 136 is configured as an aerosol injection port. The third port 136 is connected to an aerosol generator 156 to provide the aerosol challenge to the area within the shroud 130. The port 136 may be coupled to an aerosol dispersion device, such as a perforated tube 158 (shown in phantom).

After the shroud 130 is installed, the downstream and upstream sampling lines from the measuring device 164 and the aerosol generator 156 are connected. The upstream aerosol challenge concentration may be measured, as well as the overall filter efficiency, using the measuring device 164.

In one embodiment, the shroud 130 is constructed from 0.063" thick aluminum and weighs approximately 18 lbs. (8.2 kg). This allows technicians to easily mount the shroud 130 to the filter module 100 when positioned overhead.

A method for efficiency testing is also disclosed. In one embodiment the method begins from removing the grille (not shown) from the filter module 100. Next, the flexible tube 152 extending from the second port 134 in the shroud 130 is coupled to the downstream aerosol sample port 112 of the filter module 100. Once the tube 152 is connected, the shroud 130 is sealingly secured to at least one of the filter module 100, ceiling 102 and/or filter element 108 in a manner that ensures that the flow through the shroud 130 passes through the filter element 108 substantially without leakage.

The measuring device 164 is coupled to the upstream aerosol sample (first) port 132 and the downstream aerosol sample (second) port 134. The aerosol generator 156 is coupled to aerosol dispersion (third) port 136.

Flow is established through the filter element 108 using at least one of the blowers 126, 162. The aerosol generator 156 is activated to challenge the filter element 108. Upstream and downstream samples are taken using the measuring device 164 to establish the efficiency of the filter element 108. The efficiency calculations may be made using industry standards, such as National Environmental Balance Bureau (NEBB), Institute of Environmental Sciences (IES) or other testing protocol.

If the test result is acceptable, the test instruments (i.e., the generator 156 and measuring device 164) and the shroud 130 are removed. The grille is replace on the filter module 100 and the module is ready to resume normal operation.

While the foregoing is directed to embodiments of the present invention, other and further embodiments of the invention may be devised without departing from the basic scope thereof.

What is claimed is:

1. An apparatus for testing a filter element mounted in an exhaust filter module, the exhaust filter module installed in a location operable to remove air from a cleanroom, the apparatus comprising:
   a shroud having:
      walls impermeable to air flow,
      a flange disposed at one end of the walls and configured to seal against a cleanroom side face of the exhaust filter module,
      a collar disposed opposite the flange at a second end of the walls, wherein the walls, flange and collar define a plenum interior the shroud, the collar sized to provide a test air flow to the filter element from a blower without leakage, the shroud sealable to and removable from the exhaust filter module without affecting the installation of the exhaust filter module, the shroud configured to receive an aerosol challenge in an area within the shroud and deliver the aerosol challenge uniformly across the face of the exhaust filter module interfaced with the shroud;
      a first port formed through one of the walls of the shroud and configured to sample air in a volume defined between the shroud and the filter element; and
      a second port formed through one of the walls of the shroud; and
   a flexible conduit disposed in the shroud, coupled to the second port and having sufficient length to extend at least to the flange of the shroud.

2. The apparatus of claim 1 further comprising:
   an aerosol injection port formed through the shroud.

3. The apparatus of claim 2 further comprising:
   an aerosol dispersion device disposed in the shroud and coupled to the injection port.

4. The apparatus of claim 3 further comprising:
   at least one mixing element disposed in the shroud.

5. An apparatus for testing a filter element mounted in an exhaust filter module installed in an intended use location having a room side face exposed to a room, the exhaust filter module operable to filter air being exhausted from the room, the apparatus comprising:
   a removable shroud having:
      walls impermeable to air flow,
      a flange disposed at one end of the walls configured for sealing against a room side face of the filter module;
      a collar disposed opposite the flange at a second end of the walls, wherein the walls, flange and collar define a plenum interior the shroud, the collar sized to provide a test air flow to the filter element from a blower, the shroud removable from the installed filter module, the shroud configured to receive an aerosol challenge in an area within the shroud and deliver the aerosol challenge uniformly across the face of the filter module interfaced with the shroud;
      a first port formed through one of the walls of the shroud and configured to sample air in the volume defined between the shroud and the filter element; and
      a second port formed through one of the walls of the shroud; and
   a fastening element configured to secure the shroud to the filter module.

6. The apparatus of claim 5 further comprising:
   a flexible tube disposed in the shroud, the tube having one end coupled to the second port and a second end free and adapted for fluidly coupling to a ceiling side of the filter module.

7. The apparatus of claim 5 further comprising:
   an aerosol injection port formed through the shroud.

8. The apparatus of claim 7 further comprising:
   an aerosol dispersion device disposed in the shroud and coupled to the injection port.

9. The apparatus of claim 8, wherein the aerosol dispersion device comprises a perforated tube.

10. The apparatus of claim 5 further comprising:
    at least one mixing element disposed in the shroud.

11. The apparatus of claim 5, wherein the fastening element is at least one of a clamp, a stud, and a hole securing the flange to filter module.

12. The apparatus of claim 5 further comprising:
    a sealing element disposed in contact with the flange.

13. The apparatus of claim 12, wherein the sealing element is at least one of a fluid seal, a bladder, and a gasket.

14. The apparatus of claim 5, wherein the collar has a diameter of about 12 inches.

15. The apparatus of claim 5, wherein at least one of the first and second ports are configured with a quick connect-disconnect fitting.

16. An apparatus for testing a filter element mounted in an exhaust filter module installed in an intended use location having a room side face exposed to a room, the exhaust filter module operable to filter air being exhausted from the room, the apparatus comprising:
    a removable shroud having:
       walls impermeable to air flow,
       a flange disposed at one end of the walls configured for sealing against a room side face of the filter module;
       a collar disposed opposite the flange at a second end of the walls, wherein the walls, flange and collar define a plenum interior the shroud, the collar sized to provide a test air flow to the filter element from a blower, the shroud removable is configured to be disposed in its entirety in the room when the flange is engaging the room side face filter module, the shroud configured to receive an aerosol challenge in an area within the shroud and deliver the aerosol challenge uniformly across the face of the filter module interfaced with the shroud;
       a first port formed through one of the walls of the shroud and configured to sample air in the volume defined between the shroud and the filter element;
       a second port formed through one of the walls of the shroud; and
       an aerosol injection port formed through the wall of the shroud;
    an aerosol dispersion device disposed in the shroud and coupled to the injection port; and
    at least one mixing element disposed in the shroud.

* * * * *